United States Patent [19]
Willer et al.

[11] Patent Number: 5,460,669
[45] Date of Patent: Oct. 24, 1995

[54] 3-NITRAMINO-4-NITROFURAZAN AND SALTS THEREOF

[75] Inventors: Rodney L. Willer, Slidell, La.; Robert S. Day, Newark, Del.; Dennis J. Park, deceased, late of Newark, Del., by Tara J. Park, legal representative

[73] Assignee: Thiokol Corporation, Ogden, Utah

[21] Appl. No.: 82,918

[22] Filed: Jun. 28, 1993

[51] Int. Cl.$^6$ .......................... C07D 271/08; C06R 25/34
[52] U.S. Cl. .............................. 149/92; 149/45; 548/101; 548/109; 548/125
[58] Field of Search .................................. 548/125, 101, 548/109; 149/42

[56] References Cited

U.S. PATENT DOCUMENTS

| | | | |
|---|---|---|---|
| 3,740,947 | 6/1973 | Denson et al. | 60/215 |
| 3,823,249 | 8/1974 | Homewood et al. | 102/23 |
| 4,356,178 | 10/1982 | Schonafinger et al. | 424/248.54 |
| 4,416,893 | 11/1983 | Schonafinger et al. | 424/272 |
| 4,503,229 | 3/1985 | Willer | 544/343 |
| 4,822,889 | 4/1989 | Sauter et al. | 548/262 |
| 4,826,988 | 5/1989 | Sirrenberg | 548/125 |
| 5,071,495 | 12/1991 | Willer et al. | 149/19.9 |

OTHER PUBLICATIONS

Coburn, Picrylamino–Substituted Heterocycles, II Furars (1,2), J. Heterocyclic Chem., 5 83 (1968).
Willer et al., Synthesis and Properties of Methylene–Bis (Nitraminofurazans), Journal Heterocyclic Chem., 29: 1835 (1992).

Willer et al. Synthesis of High–Nitrogen Content Heterocyclic Nitramines and Energetic Internal Plasticizers, Final Report for Feb., 1985–Mar., 1987, (Jun. 1987).

Tselinskii et al., Acid–Base Properties of 1,2–5–Oxadiazoles, Journal of Organic Chemistry USSR 228 (1981); and 1835 (1922).

Solodyuk et al., Oxidation of 3–4–Diaminofurazan by Some Peroxide Reagents, Journal of Organic Chemistry USSR, 756 (1981).

*Primary Examiner*—Donald P. Walsh
*Assistant Examiner*—Anthony R. Chi
*Attorney, Agent, or Firm*—Madson & Metcalf; Ronald L. Lyons

[57] ABSTRACT

The energetic salts of 3-nitramino-4-nitrofurazan have a desirable combination of desirable properties such as sufficiently high densities, and low or no hydrogen content. The salts are useful as ingredients in various propellant, explosive, gassifier, and pyrotechnic compositions. 3-Nitramino-4-nitrofurazan is itself a useful energetic compound and is also useful in the synthesis of still further energetic compounds.

11 Claims, No Drawings

3-NITRAMINO-4-NITROFURAZAN AND SALTS THEREOF

FIELD OF THE INVENTION

The present invention concerns the novel compound 3-nitramino-4-nitrofurazan and the salts thereof. The compound and its energetic salts are useful as ingredients in energetic compositions including propellants, explosives, gassifiers and pyrotechnics.

DESCRIPTION OF THE ART

There would appear to be scant literature references which are relevant to the present inventions.

Certain aminofurazans and the acid-base properties thereof, are described in *Khim. Getero. Sod.*, 321–324 (1981).

Oxidation of 3,4-diaminofurazan by certain peroxide reagents is described in *Zhurnal Organ. Khimii*, 17:861–65 (1981)

The synthesis of certain picrylamino- and nitro-substituted furazans and bifurazanyls is disclosed in *J. Heterocyclic Chem.*, 5:83 (1968).

Methylene bis(3-aminofurazans) and methylene bis 3-(nitramino furazans) with methyl and nitro substituents at the 4 and 4'-positions are described in *J. Heterocyclic Chemistry*, 29:1835 (1992).

3-Nitramino-4-nitrofurazan, means for making it, and its utilities are not described in this literature.

SUMMARY OF THE PRESENT INVENTION

The present invention comprises 3-nitramino-4-nitrofurazan and salts thereof.

An energetic salt of 3-nitramino- 4-nitrofurazan has a desirable combination of sufficiently high crystalline density, low or no hydrogen content, and an unexpectedly high temperature of decomposition which makes such a salt suitable for use as an ingredient in the production of various energetic compositions such as propellants, explosives, gassifiers, and pyrotechnics. The water soluble salts can, for instance, be used in making liquid gun propellants.

DETAILED DESCRIPTION OF THE INVENTION

3-Nitramino-4-nitrofurazan can be depicted by the following formula:

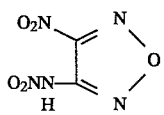

The compound has a density of about 1.93 g/ml.

The energetic salts of 3-nitramino- 4-nitrofurazan comprise useful ingredients for use in energetic compositions. These salts are exemplified by the formula $MX_n$ wherein M is a cation, X is the anion of 3-nitramino- 4-nitrofurazan, and n is an integer corresponding to the valence of the cation X. The value of n depends on the valence of M, and can be, for instance, 1, 2, 3, 4, or higher.

When M is a metal cation, the metal thereof can be selected from the group consisting of metals from groups IA, IIA, IIIA, IVA, VA, VIA, IB, IIB, IIIB, IVB, VB, VIIB, VIIIB, and the Lanthanide Elements (51–71) of the Periodic Table. Advantageously, M is selected from the group consisting of Li, Na, K, Rb, Cs, Ca, Ba, Sr, Mg, Cu, Ag, Au, Zn, Cd, Hg, Al, Sc, Y, Ga, B, In, Lanthanide Elements (57–71), Ti, Zr, Hf, Ge, Sn, V, Nb, Ta, Cr, Mo, W, Mn, Tc, Re, Fe, Co, Ni, Ru, Rh, Pd, Os, Ir, Pt, and mixtures thereof.

The cation of an energetic salt of 3-nitramino- 4-nitrofurazan can be non-metallic. Non-metallic cations can be nitrogen and/or carbon containing. The class of non-metallic cations includes nitrogen-containing and carbon-containing cations such as, for example, ammonium, hydroxyl ammonium, dinitroazetidium, hydrazinium, guanidinium and $(C(CH_2NH_3)_4)^{+4}$, among others.

Salts according to the present invention can have increased electron densities on the nitramino functionality and exhibit an attendant desired but unexpected enhanced thermal stability. Typifying this unexpected combination of properties are, for instance, the ammonium salt which has a decomposition temperature of about 121° C., the hydroxylammonium salt which has a decomposition temperature of about 163° C. and a hydrazinium salt which has a decomposition temperature of about 184° C. By way of comparison, a methylene-bis compound described in *J. Heterocyclic Chem.* 29:1835 (1992) possesses insufficient thermal stability and decomposes at less than 100° C. Metal salts according to the present invention are also sufficiently thermally stable to be useful in energetic applications. For instance, illustrative of the mono-valent metal salts are the potassium salt which is thermally stable to about 206° C., and the sodium salt which is relatively stable even above 100° C.

The present salts of 3-nitramino-4-nitrofurazan are also generally relatively dense materials. The hydroxylammonium salt has a density of about 1.875 g/ml.

Certain energetic compositions containing at least one salt according to the present invention are superior to comparably formulated energetic compositions containing CL-20.

3-Nitramino-4-nitrofurazan is obtainable by nitrating 3-amino-4-nitrofurazan with a suitable nitrating reagent.

The 3-amino-4-nitrofurazan starting material can be obtained, for instance, by treating 3,4-diaminofurazan with peroxytrifluoroacetic acid to obtain a blue-green solution. That solution is heated under reflux until light yellow. Further heating will reduce the yield. The light yellow solution is, in turn, treated with $Na_2CO_3$ (aqueous) and the desired 3-amino- 4-nitrofurazan is extracted from the treated solution. The extrated 3-amino-4-nitrofurazan can be further purified by recrystallization. A synthesis starting from 3,4-diaminofurazan is described in, for example, *J. Heterocyclic Chem.*, 5:83 (1968), the disclosure of which is incorporated herein by reference.

Various strong nitrating reagents can, in principle, be used and include nitric acid—acetic anhydride or dinitrogen pentoxide ($N_2O_5$) in methylene chloride. The latter reagent is preferred, and can be prepared according to *Inorganic Synthesis, IX*:83–88 (1967), the disclosure of which is incorporated herein by reference.

The concentration of the nitrating reagent does not appear to be critical. The actual concentration will be suitably selected as a function of various pragmatic objectives such as minimization of solvents.

The nitration is generally conducted in the presence of a non-reactive solvent. Illustrative of the various suitable solvents are methylene chloride, chloroform, carbon tetrachloride, and dichloroethane. The solvent for the nitration can also serve as the solvent for the nitrating reagent.

The nitration can be conducted across a wide temperature range. The temperature is not particularly critical. An exemplary temperature range is, for instance, from sub-ambient, such as −30° C., to above 0° C. such as 15° C. Sub-ambient temperatures can be obtained according to various means known to those skilled in the art such as an ice bath, brine chiller or, for instance, nitromethane/$CO_2$.

The reactions are, as a matter of course, conducted anhydrous and also, preferably, in an inert atmosphere such as nitrogen.

Metal salts of 3-nitramino-4-nitrofurazan are readily obtainable according to procedures known to those skilled in the art. Metal salts can be obtained, for instance, by allowing a metal hydroxide or oxide in a solvent, such as methanol, to react with 3-nitramino-4-nitrofurazan. The reactants can be combined at a rate which permits control over the exothermic reaction.

Non-metallic salts of 3-nitramino-4-nitrofurzan can be facilely produced in an analogous manner.

Other energetically useful compounds can be derived or synthesized from 3-nitramino-4-nitrofurazan.

An exemplary liquid gun propellant composition can comprise an energetically effective amount of a salt of 3-nitramino- 4-nitrofurazan and water. Such a mono-propellant can exhibit unexpectedly enhanced impetus values compared to a comparable formulation based on hydroxylammonium nitrate ("HAN") and triethanol amine ("TEAN"). For instance, a liquid gun propellant containing an energetic salt of 3-nitramino- 4-nitrofurazan, such as the hydroxylammonium salt (60 wt. %), can have approximately the same impetus value obtainable from a liquid gun propellant containing HAN (60 wt. %) and TEAN (20 wt. %).

Conventional HAN/TEAN-based liquid gun propellants can be moderately energetically tailored by including an energetically enhancing amount of at least one salt of 3-nitramino-4-nitrofurazan as a supplement to the energetic components (HAN and TEAN).

EXAMPLES

The following non-limiting examples describe the invention in further detail.

$^1$H-NMR spectra reported herein were recorded (Varian EM-360A NMR spectrometer) and referenced the TMS. IR spectra reported herein were also recorded (Nicolet 5DXB FTIR spectrometer) as either films (liquids) or KBr pellets (solid). The melting points, decomposition points, were measured using a DuPont 910 DSC coupled to a TA 2200 thermal analyzer at 10° C./min. Elemental analyses were also conducted as reported herein.

EXAMPLE 1

To a dry 50 ml r.b. flask cooled to −30° C. was added 3.015 g of a 1M $N_2O_5$ in methylene chloride solution. 3-Amino-4-nitrofurazan ("ANF"; 0.10 g, 0.77 mole) was then added in small portions over 15 minutes. The temperature was raised to 0° C. and the solution was stirred for one hour. The methylene chloride, excess $N_2O_5$, and nitric acid were removed in vacuo. Ammonium hydroxide (1 g) was added and the excess ammonia and water removed in vacuo. The product was titrated with a mixture of ether/ethylacetate to yield a crystalline product (0.120 g, 63 mmoles, 82% yield). DSC analysis showed a sharp exotherm at 133° C. The product was recrystallized from ethyl acetate to yield off white crystals which were subjected to x-ray structure analysis. FT-IR analysis (KBr) showed absorptions at 3207 (b), 1584 (s), 1467 (m), 1418 (s), 1346 (m), 1292 (s), 1045 (w), 1009 (w), 934 (w), 830 (w), 800 (m), 780 (2), cm$^{-1}$.

EXAMPLE 2

3-Nitramino-4-Nitrofurazan From 3-Amino-4-Nitrofurazan

A clean, dry, 300 ml 3 neck round bottom flask was equipped with a vacuum adapter (for $N_2$), rubber septa, magnetic stirring bar and thermocouple. The flask was charged with 99.94 g (0.09M) 10% $N_2O_5$ in anhydrous $CH_2Cl_2$ via syringe. It was immediately set in a nitromethane/$CO_2$ bath and cooled to −20° C., as the septa was exchanged for a glass stopper. Aminonitrofurazan ("ANF"; 9.75 grams; 0.75M) was preweighed into a glass vial. The ANF was added over an 8 minute period not exceeding −17° C. All residue was rinsed down with 2 mls anhydrous $CH_2Cl_2$. The bath was exchanged for an ice/water bath and the mixture was stirred for 3.5 hrs, not exceeding +10° C. The reaction mixture was then transferred to a one neck tarred round bottom flask, and the solvent was removed in vacuo at ambient and crystals were obtained. The crystals were then placed under high vacuum for ½ hour to remove trace ($HNO_3$), yield 95–100% of theoretical. The product was recrystallized using 16.2 ml of dry chloroform per gram of crude product. A slurry in chloroform was formed and was stirred at 41° C. until all crystals dissolved, then set into a refrigerator-freezer at −20° C. for 16 hrs. The crystals were collected (84% theoretical yield) on a paper filter using glass spatulas for transfer. A discoloration was noted when stainless steel was used in a high humidity situation. DSC analysis: melt at 57° C. decomposition temperature 101° C. Crystals which were recrystallized twice were more needle like with DSC melt at 60° C., decomposition 101.5° C. The crystals had a density (gas picnometer) of 1.93 g/cc. FTIR analysis (KBR) 3278 (s); 1631, 1606 (d); 1549, 1503 (d); 1383, 1337 (d). $\Delta H_c$ 1567/g, $\Delta H_f$+60 Kcal/mole.

EXAMPLE 3

Hydroxylammonium 3-Nitroamino-4-Nitrofurazan

A dry clean 250 ml 3 neck round bottom flask equipped with a nitrogen port, magnetic stirring bar, thermocouple was set into an ice bath. 3-Nitroamino-4-nitrofurazan (5.0 grams 0.0285M) was added with 40 ml distilled water. Hydroxyl amine (HA) (11.5% wt in water) was preweighed into a vial, (8.20 grams 0.94 grams HA; 0.0285M). HA was added over three minutes with a pipet at a temperature not exceeding 3° C. The vial was rinsed with 2 mls $H_2O$ for quantitative transfer of its contents. Following ten minutes the reaction mixture was stirred cold, then the ice bath was withdrawn and stirred at ambient for 1½–2 hrs. After transfer to a tarred one neck flask, the water was removed in vacuo at 40° C. to obtain crystals. Crystals were then placed under high vacuum for at least 8 hrs., giving 101% theoretical yield. The product was recrystallized using 9.87 ml of nitromethane per gram of crude product nitromethane. A slurry was formed and was stirred at 63° C., then a few drops of methanol was added and all crystals went into solution. The solution was then set into a refrigerator-freezer at −20° C. for 16 hrs. Sparkly pearlescent flaky crystals were collected on paper and dried to give 84% theoretical yield. DSC: melt 132° C., exothermic decomposition 162.9° C. FTIR, 3200–2700 (m), 1582 (s), 1510 (s), 1336, 1303 (d). Empirical formula, $C_2H_4N_6O_6$, density, (x-ray analysis) 1.875 g/cc. $\Delta H_c$ 1648 cal/g, $\Delta H_f$+18 Kcal/mole.

EXAMPLE 4

Hydrazinium 3-Nitramino-4-Nitrofurazan

Into a clean 250 ml 3 neck round bottom flask equipped with a nitrogen port, magnetic stirring bar, and thermocouple was placed 3-nitroamino- 4-nitrofurazan ("ANF"; 4.44 grams 0.025M). Thirty-five mls of distilled water was then added and the flask set into an ice bath. Fuming hydrazine (95%; 0.942 g; 0.028M) was preweighed into a vial, then added over three minutes while not letting the reaction temperature exceed +8° C. The reaction mixture was kept cold for 10 minutes, then the ice bath was withdrawn and the reaction mixture was stirred 2.5 hrs. After transfer to a tarred one neck flask, the water was removed in vacuo at 40° C. to obtain crystals (94% yield). The crystals were dissolved in approximately 200 ml THF at 40° C. then the amount of solvent present was reduced and thereafter the solution was refrigerated at −20° C. for 16 hrs. The resulting yellow green crystals were collected and placed over high vacuum (68.5% theoretical yield). DSC: decomposition at 184° C. FTIR 3500–3000 (m), 1583 (s), 1467, 1422, 1395, 1348, 1296 (m). The density of the hydrate (X-ray analysis) was 1,704 g/ml.

EXAMPLE 5

Ammonium Salt of 3-Nitramino-4-Nitrofurazan

A clean 3 neck round bottom flask was equipped with magnetic stirring bar, thermocouple and set into an ice bath. 3-Nitroamino-4-nitrofurazane (0.5 g; 0.0029M) was added with 4 ml distilled $H_2O$. Ammonium hydroxide, (29%; 0.20 g; 0.006M) was preweighed, then added via syringe over two minutes while the temperature did not exceed 7° C. The mixture was stirred cold for 10 minutes, then stirred an additional hour at ambient. The mixture transferred to a tarred one neck flask, and the water was removed in vacuo at 38° C. Upon completion of high vacuum, the yield of crystals was calculated as 105% of theoretical. The crystals were dissolved in a ethylacetate and precipitated by an equal amount of hexanes at − 20 C. The resulting crystals were collected (65% yield). DSC: decomposition 121° C. FTIR: 3300– 3000 (m), 1579 (s), 1464, 1423, 1390 (t), 1347 (s), 1281, 1250 (d).

EXAMPLE 6

Potassium 3-Nitramino-4-Nitrofurazan

A clean 3 neck round bottom flask was equipped with magnetic stirring, thermocouple, and set into an ice bath. 3-Nitroamino-4-nitrofurazane (0.5 g; 0.0029M) was added with 4 ml distilled $H_2O$. Potassium hydroxide (0.1957 g; 0.003M) was preweighed in a vial then dissolved in 2 ml distilled $H_2O$. This was then added slowly over three minutes not exceeding 10° C. The mixture was stirred cold for 10 minutes, then stirred an additional hour at ambient. After transfer to a tarred 1 neck flask, the water was removed in vacuo at 38° C., upon completion of high vacuum treatment, the yield of crystals was 102% of theoretical. DSC: exothermic peaks at 206° C., 210° C., and 437° C. FTIR: 3500 (broad), 1577 (s), 1458, 1425, 1393, 1345, 1289 (m).

EXAMPLE 7

Sodium 3-Nitramino-4-Nitrofurazan

A 3 neck round bottom flask was equipped with magnetic stirring bar, thermocouple, and set in an ice bath. 3-Nitramino-4-nitrofurazan (0.5 g; 0.002M) was added with 4 ml distilled $H_2O$. Sodium Hydroxide (0.1263 g; 0.003M) was preweighed into a vial and dissolved in 2 ml distilled $H_2O$. The sodium hydroxide solution was slowly added to the 3-nitramino-4-nitrofurazan over four minutes while the temperature did not to exceed 10° C. The mixture was initially stirred 10 minutes cold, and was then stirred another one hour at ambient. Upon transfer a one neck flask, the water was removed in vacuo. After a period of high vacuum, circular crystals were noted with a yield of 105% theoretical DSC: melt 103° C., strong exothermic decomposition peak at 129.5° C., several weaker ones at 136° C., 147° C., 162° C., and 208° C. FTIR: 3578, 3513 (d), 1645, 1582, 1537 (t), 1471, 1442 (d), 1351, 1299, 1267 (t).

EXAMPLE 8

Dinitroazetidinium 3-Nitramino-4-Nitrofurazan

A clean 3 neck round bottom flask was equipped with magnetic stirring, thermocouple, and nitrogen and placed into an ice bath. 3-Nitroamino- 4-nitrofurazan (1.75 grams; 0.01M) is added to 5 mls dry methanol. Dinitroazetidinium (1.47 grams; 0.01 mol) is added slowly over 10 minutes not exceeding 10° C. The resulting mixture is stirred cold for 10 minutes, then the mixture is stirred for an additional hour at room temperature. After transfer to a tarred one neck flask, the solvent is removed in vacuo at 35° C. Recrystallization followed.

EXAMPLE 9

Guanidinium 3-Nitramino-4-Nitrofurazan

A clean dry 3 neck round bottom flask was equipped with magnetic stirring bar, thermocouple, and nitrogen inlet is placed in an ice bath. 3-Nitroamino- 4-nitrofurazan (1.75 grams; 0.1 mol) was added with 5 mls dry methanol. Guanidine (0.59 grams; 0.01 mol) was preweighed into a vial and dissolved in 5 ml dry methanol. The guanidine-containing mixture was added over 5 minutes while the temperature did not exceed 10° C. The resulting mixture was stirred cold for 10 min, and then stirred for an additional hour at ambient. After transfer to a tarred one neck flask, the solvent was removed in vacuo at 35° C. After a period of high vacuum, the yield of crystals was 100% of theoretical. DSC: exothermic peak at 90.96° C. FTIR: 3517, 3413, 3270, 3212 (m), 1660 (d), 1576 (s), 1386, 1344, 1311 (t).

EXAMPLE 10

Zinc 3-Nitramino-4-Nitrofurazan

A three neck round bottom flask was equipped with a magnetic stirring bar and thermocouple and then set in an ice bath. 3-Nitramino- 4-nitrofurazan (0.546 g, 0.00312M) was added with 4.3 ml distilled water. Zinc oxide (0.1396 g; 0.0017M) was slowly added over two minutes, at a temperature not exceeding 7° C. The mixture was stirred cold for 10 minutes, then stirred an additional hour at ambient. Upon transfer to a one neck flask, the water was reduced in vacuo, after which high vacuum followed yielding 107% theoretical of a paste. DSC: exothermic peak at 111° C., 250° C. and 314° C. FTIR: 3563 (Broad), 1583 (s), 1467, 1423, 1348, 1297 (m).

What we claim is:

1. 3-nitramino-4-nitrofurazan and salts thereof wherein a salt has the formula $MX_n$ wherein M is a cation, X is the anion of 3-nitramino- 4-nitrofurazan, and n is an integer corresponding to the valence of the cation M.

2. A salt according to claim 1, wherein M is a metal cation.

3. A salt according to claim 2, wherein the metal cation is mono-valent.

4. A salt according to claim 3, wherein the metal cation is potassium or sodium.

5. A salt according to claim 1, wherein M is a non-metallic cation.

6. A salt according to claim 5, wherein M is selected from the group consisting of $NH_4^+$, $(NH_3OH)^+$, $(NH_3NH_2)^+$, and dinitroazetidium.

7. A liquid gun propellant composition comprising a salt of 3-nitramino- 4-nitrofurazan, wherein said salt has the formula $MX_n$, wherein M is a cation, X is the anion of 3-nitramino- 4-nitrofurazan, and n is an integer corresponding to the valence of the cation M.

8. A liquid gun propellant composition according to claim 7, wherein M is a non-metallic cation.

9. A liquid gun propellant composition according to claim 8, wherein M is selected from the group consisting of $NH_4^+$, $(NH_3OH)^+$, $(NH_3NH_2)^+$, and dinitroazetidium.

10. A salt according to claim 5, wherein M is selected from the group consisting of guanidinium and $(C(CH_2NH_3)_4)^{+4}$.

11. The hydroxylammonium salt of 3-nitramino-4-nitrofurazan.

* * * * *